United States Patent
Kojima et al.

(10) Patent No.: US 9,029,428 B2
(45) Date of Patent: May 12, 2015

(54) OIL-IN-WATER SILICONE EMULSION COMPOSITION

(75) Inventors: Kazuhiko Kojima, Ichihara (JP); Masaru Ozaki, Ichihara (JP); Seiji Hori, Chiba (JP)

(73) Assignee: Dow Corning Toray Co., Ltd., Chiyoda-Ku, Tokyo (JP)

( * ) Notice: Subject to any disclaimer, the term of this patent is extended or adjusted under 35 U.S.C. 154(b) by 0 days.

(21) Appl. No.: 13/806,886

(22) PCT Filed: Jun. 29, 2011

(86) PCT No.: PCT/JP2011/065421
§ 371 (c)(1),
(2), (4) Date: Feb. 21, 2013

(87) PCT Pub. No.: WO2012/002571
PCT Pub. Date: Jan. 5, 2012

(65) Prior Publication Data
US 2013/0143989 A1 Jun. 6, 2013

(30) Foreign Application Priority Data
Jul. 2, 2010 (JP) ................................ 2010-151676

(51) Int. Cl.
| C08J 3/03 | (2006.01) |
| C09D 183/08 | (2006.01) |
| C09D 183/06 | (2006.01) |
| C08G 77/16 | (2006.01) |

(52) U.S. Cl.
CPC .............. *C09D 183/08* (2013.01); *C08G 77/16* (2013.01); *C08J 3/03* (2013.01); *C08J 2383/06* (2013.01); *C08J 2383/08* (2013.01); *C09D 183/06* (2013.01)

(58) Field of Classification Search
None
See application file for complete search history.

(56) References Cited

U.S. PATENT DOCUMENTS

| 2,891,920 | A | 6/1959 | Hyde et al. |
| 3,294,725 | A | 12/1966 | Findlay et al. |
| 3,419,593 | A | 12/1968 | Willing |
| 3,445,420 | A | 5/1969 | Kookootsedes et al. |
| 3,715,334 | A | 2/1973 | Karstedt |
| 3,814,730 | A | 6/1974 | Karstedt |
| 3,819,530 | A | 6/1974 | Ratledge et al. |
| 3,839,388 | A | 10/1974 | Nitzsche et al. |
| 3,923,705 | A | 12/1975 | Smith |
| 3,989,667 | A | 11/1976 | Lee et al. |
| 4,221,688 | A * | 9/1980 | Johnson et al. ............... 524/251 |
| 4,311,695 | A | 1/1982 | Starch |
| 4,312,801 | A | 1/1982 | Hiriart Bodin et al. |
| 4,404,035 | A | 9/1983 | Ona et al. |
| 4,427,811 | A * | 1/1984 | Elias et al. ...................... 524/96 |
| 4,564,693 | A | 1/1986 | Riederer |
| 4,614,758 | A | 9/1986 | Schwabe et al. |
| 4,701,490 | A | 10/1987 | Buckhardt et al. |
| 4,725,658 | A | 2/1988 | Thayer et al. |
| 4,769,405 | A | 9/1988 | Kondo et al. |
| 4,788,001 | A | 11/1988 | Narula |
| 4,990,556 | A | 2/1991 | Shimizu et al. |
| 4,990,561 | A | 2/1991 | Yoshioka |
| 5,035,832 | A | 7/1991 | Takamura et al. |
| 5,039,724 | A | 8/1991 | Demlehner et al. |
| 5,110,865 | A * | 5/1992 | Ona et al. ...................... 524/838 |
| 5,133,897 | A | 7/1992 | Balzer |
| 5,175,325 | A | 12/1992 | Brown et al. |
| 5,189,102 | A | 2/1993 | Tsubuko et al. |
| 5,262,087 | A | 11/1993 | Tachibana et al. |
| 5,300,608 | A | 4/1994 | Chu et al. |
| 5,403,909 | A | 4/1995 | Rubinsztajn |
| 5,434,215 | A | 7/1995 | Sankaran et al. |
| 5,457,220 | A | 10/1995 | Razzano |
| 5,503,755 | A | 4/1996 | Danner |
| 5,504,150 | A | 4/1996 | Gilson et al. |
| 5,603,940 | A | 2/1997 | Candau et al. |
| 5,633,303 | A | 5/1997 | Kondo et al. |

(Continued)

FOREIGN PATENT DOCUMENTS

| CN | 1230547 | 10/1996 |
| CN | 101073537 A | 11/2007 |

(Continued)

OTHER PUBLICATIONS

International Search Report for Application No. PCT/EP2007/008753 dated May 15, 2008, 3 pages.*
International Search Report for Application No. PCT/EP2007/060586 dated Jun. 4, 2008, 3 pages.*
International Search Report for Application No. PCT/EP2010/054220 dated Oct. 4, 2010, 4 pages.*
International Search Report for Application No. PCT/EP2010/054221 dated Jan. 14, 2011, 6 pages.*
International Search Report for Application No. PCT/US2007/021562 dated Feb. 8, 2008, 3 pages.*
International Search Report for Application No. PCT/EP2010/054219 dated Oct. 4, 2010, 4 pages.*
International Search Report for Application No. PCT/JP2010/054267 dated Sep. 30, 2010, 3 pages.*

(Continued)

*Primary Examiner* — Marc Zimmer
(74) *Attorney, Agent, or Firm* — Howard & Howard Attorneys PLLC

(57) ABSTRACT

Provided is an oil-in-water silicone emulsion composition that has a low silicone oligomer content, and that can form, even without the use of an organotin compound as a curing catalyst, a cured film that exhibits satisfactory strength and satisfactory adherence to a substrate, through the removal of water fraction. An oil-in-water silicone emulsion composition comprising (A) 100 mass parts of a polyorganosiloxane that contains in each molecule at least two groups selected from the group consisting of a silicon-bonded hydroxyl group, alkoxy group, and alkoxyalkoxy group, (B) 0.1 to 200 mass parts of a colloidal silica, (C) 0.1 to 100 mass parts of an aminoxy group-containing organosilicon compound that has in each molecule an average of two silicon-bonded aminoxy groups, (D) 1 to 100 mass parts of an ionic emulsifying agent, (E) 0.1 to 50 mass parts of a non-ionic emulsifying agent, and (F) 10 to 500 mass parts of water.

17 Claims, No Drawings

(56) References Cited

U.S. PATENT DOCUMENTS

| | | |
|---|---|---|
| 5,674,937 A | 10/1997 | Berg et al. |
| 5,830,483 A | 11/1998 | Seidel et al. |
| 5,861,451 A | 1/1999 | Schroeder et al. |
| 5,888,485 A | 3/1999 | O'Lenick, Jr. et al. |
| 5,914,362 A | 6/1999 | Brecht et al. |
| 5,925,469 A | 7/1999 | Gee et al. |
| 5,973,068 A | 10/1999 | Yamaya et al. |
| 5,994,459 A * | 11/1999 | Berg et al. ............. 524/837 |
| 6,001,928 A | 12/1999 | Harkness et al. |
| 6,054,548 A | 4/2000 | Currie et al. |
| 6,258,891 B1 | 7/2001 | Hoxmeier |
| 6,328,983 B1 | 12/2001 | Afriat |
| 6,362,280 B1 | 3/2002 | Lences et al. |
| 6,448,196 B1 | 9/2002 | Eglin et al. |
| 6,468,513 B1 | 10/2002 | Murphy et al. |
| 6,610,788 B1 * | 8/2003 | Takakura et al. ......... 525/276 |
| 6,737,444 B1 | 5/2004 | Liu |
| 7,041,088 B2 | 5/2006 | Nawrocki et al. |
| 2003/0191244 A1 | 10/2003 | Yu |
| 2004/0210074 A1 | 10/2004 | Hupfield et al. |
| 2005/0143282 A1 | 6/2005 | Creutz et al. |
| 2007/0269390 A1 | 11/2007 | Inoue |
| 2008/0114143 A1 | 5/2008 | Brothers et al. |
| 2009/0042043 A1 | 2/2009 | Joseph et al. |
| 2009/0114327 A1 | 5/2009 | Breunig |
| 2009/0215944 A1 | 8/2009 | Maton et al. |
| 2010/0093598 A1 | 4/2010 | Davio et al. |
| 2010/0137454 A1 | 6/2010 | Barmes et al. |
| 2011/0319557 A1 | 12/2011 | Kojima et al. |
| 2012/0004354 A1 | 1/2012 | Kojima et al. |
| 2012/0027708 A1 | 2/2012 | Durand et al. |
| 2012/0077729 A1 | 3/2012 | Davio et al. |

FOREIGN PATENT DOCUMENTS

| | | |
|---|---|---|
| CN | 101247934 A | 8/2008 |
| EP | 0200916 A2 | 11/1986 |
| EP | 0215470 A2 | 3/1987 |
| EP | 0382365 A2 | 8/1990 |
| EP | 0722972 A1 | 7/1996 |
| EP | 0736562 A2 | 10/1996 |
| EP | 0739929 A2 | 10/1996 |
| EP | 0802231 A2 | 10/1997 |
| EP | 0842974 A1 | 5/1998 |
| EP | 0915122 A1 | 5/1999 |
| EP | 1029897 A1 | 8/2000 |
| EP | 1314415 A1 | 5/2003 |
| EP | 1447423 A1 | 8/2004 |
| EP | 1466935 A1 | 10/2004 |
| EP | 1557435 A1 | 7/2005 |
| EP | 1671673 A1 | 6/2006 |
| GB | 895091 A | 5/1962 |
| GB | 918823 A | 2/1963 |
| GB | 2056473 A | 3/1981 |
| GB | 2252975 A | 8/1992 |
| JP | 56-016553 A | 2/1981 |
| JP | 56016553 A | 2/1981 |
| JP | 59-152972 A | 8/1984 |
| JP | 59152972 A | 8/1984 |
| JP | 06-073291 A | 3/1994 |
| JP | 8302023 A | 11/1996 |
| JP | 8302194 A | 11/1996 |
| JP | H08-325456 A | 12/1996 |
| JP | 09-165554 A | 6/1997 |
| JP | 10140136 A | 5/1998 |
| JP | 10-168393 A | 6/1998 |
| JP | 11-193349 A | 7/1999 |
| JP | 11193349 A | 7/1999 |
| JP | 11-222554 A | 8/1999 |
| JP | 2000-026726 | 1/2000 |
| JP | 2002-088243 | 3/2002 |
| JP | 2002-088243 A | 3/2002 |
| JP | 2006-515383 A | 5/2006 |
| JP | 2010235930 A | 10/2010 |
| JP | 2010235931 A | 10/2010 |
| WO | WO 01/25389 A1 | 4/2001 |
| WO | WO 01/49774 A2 | 7/2001 |
| WO | WO 01/49789 A2 | 7/2001 |
| WO | WO 01/79330 A1 | 10/2001 |
| WO | WO 03/082356 A2 | 10/2003 |
| WO | WO 2004/084844 A2 | 10/2004 |
| WO | WO 2005/016998 A2 | 2/2005 |
| WO | WO 2006/106362 A1 | 10/2006 |
| WO | WO 2008/043512 A2 | 4/2008 |
| WO | WO 2008/045427 A1 | 4/2008 |
| WO | WO 2008/090458 A1 | 7/2008 |
| WO | WO 2008/110590 A1 | 9/2008 |
| WO | WO 2009/021562 A2 | 2/2009 |
| WO | WO 2010/104185 * | 9/2010 |
| WO | WO 2010/104185 A2 | 9/2010 |
| WO | WO 2010/104186 A2 | 9/2010 |
| WO | WO 2010/115781 A2 | 10/2010 |
| WO | WO 2010/115782 A2 | 10/2010 |
| WO | WO 2010/115783 A2 | 10/2010 |

OTHER PUBLICATIONS

International Search Report for Application No. PCT/JP2010/054268 dated Oct. 4, 2010, 3 pages.*
English language abstract and translation for JP 06-073291 extracted from espacenet.com on Mar. 12, 2013, 42 pages.
English language abstract not found for JP 8302023. However see English language equivalent US 5,674,937. Original document extracted from espacenet.com on Mar. 12, 2013, 20 pages.
English language abstract not found for JP 8302194. However see English language equivalent EP 0739929. Original document extracted from espacenet.com on Mar. 12, 2013, 14 pages.
English language abstract and translation for JP 09-165554 extracted from espacenet.com on Mar. 12, 2013, 38 pages.
English language abstract for JP 10140136 extracted from espacenet.com on Mar. 12, 2013, 15 pages.
English language abstract and translation for JP 10-168393 extracted from espacenet.com on Mar. 12, 2013, 38 pages.
English language abstract for JP 11193349 extracted from espacenet.com on Mar. 12, 2013, 10 pages.
English language abstract for JP 59152972 extracted from espacenet.com on Mar. 12, 2013, 7 pages.
English language abstract and translation for JP 2002-088243 extracted from espacenet.com on Mar. 12, 2013, 36 pages.
English language abstract for JP 2010235930 extracted from espacenet.com on Mar. 12, 2013, 16 pages.
English language abstract for JP 2010235931 extracted from espacenet.com on Mar. 12, 2013, 14 pages.
International Search Report for Application No. PCT/JP2011/065421 dated Jul. 10, 2011, 5 pages.
English language abstract for EP 0215470 extracted from the espacenet.com database on Jul. 8, 2013, 14 pages.
English language abstract not available for JP H08-325456; however, see English language equivalent US 5,504,150. Orginal document extracted from the espacenet.com database on Jul. 8, 2013, 12 pages.
English language abstract and machine-assisted English translation for JP 11-222554 extracted from the PAJ database on Jul. 8, 2013, 36 pages.
English language abstract not available for JP 2006-515383; however, see English language equivalent US 6,737,444. Original document extracted from the espacenet.com database on Jul. 8, 2013, 15 pages.
H.H. Chuah et al., "Poly(trimethylene terephthalate) molecular weight and Mark-Houwink equation", Polymer 42 (2001) 7137-7139.
English language abstract for EP 1671673 extracted from the espacenet.com database on Mar. 7, 2012, 30 pages.
English language abstract and translation for JP 2000-026726 extracted from the PAJ database on Mar. 7, 2012, 40 pages.
English language abstract for CN 101073537 extracted from the espacenet.com database on Apr. 16, 2013, 25 pages.
English language abstract for CN 101247934 extracted from espacenet.com database on Apr. 16, 2013. Also, see English language equivalent US 2009/0114327. Original document extracted from the espacenet.com database on Apr. 16, 2013, 24 pages.

(56) References Cited

OTHER PUBLICATIONS

Edens et al., "Applications of Block Copolymer Surfactants", Development in Block Copolymer Science and Technology, Wiley, US, Jan. 1, 2004, pp. 326-340.

Holmberg, "Applications of block copolymers", Jan. 1, 2000, Amphiphilic Block Copolymers self-assembly and applications, 15 pages.

English language abstract for JP 2002-088243 extracted from the Searching PAJ database on Apr. 16, 2013, along with Machine Translation, 36 pages.

English language abstract and translation for JP 06-073291 extracted from the PAJ database on Feb. 10, 2012, 42 pages.

English language abstract and translation for JP 09-165554 extracted from the PAJ database on Feb. 10, 2012, 29 pages.

English language abstract and translation for JP 10-168393 extracted from the PAJ database on Feb. 10, 2012, 38 pages.

English language abstract and translation for JP 11-193349 extracted from the PAJ database on Feb. 10, 2012, 31 pages.

English language abstract for JP 59-152972 extracted from the espacenet.com database on Feb. 10, 2012, 6 pages.

* cited by examiner

OIL-IN-WATER SILICONE EMULSION COMPOSITION

RELATED APPLICATIONS

This application is the National Stage of International Patent Application No. PCT/JP2011/065421, filed on Jun. 29, 2011, which claims priority to and all the advantages of Japanese Patent Application No. 2010-151676, filed on Jul. 2, 2010, the content of which is incorporated herein by reference.

TECHNICAL FIELD

The present invention relates to an oil-in-water silicone emulsion composition; and particularly relates to an oil-in-water silicone emulsion composition that contains colloidal silica; and more particularly relates to a colloidal silica containing oil-in-water silicone emulsion composition that has a low silicone oligomer content, and that, even without the use of an organotin compound as the curing catalyst, is capable of forming a cured film having rubbery elasticity as the result of the removal of water fraction.

BACKGROUND ART

Oil-in-water silicone emulsion compositions that through the removal of the water fraction form a cured film having mold releasability, peeling releasability, water repellency, stain resistance, or heat resistance are used in paints, paper coating agents, mold release agents, peeling release agents, textile treatment agents, cosmetics, and so forth. There has been demand in recent years for an oil-in-water silicone emulsion composition that does not employ an organotin compound as the curing catalyst. A composition comprising a hydroxyl containing diorganosiloxane, a silicone resin, and an aminoxy group terminated diorganosiloxane (refer to Japanese Unexamined Patent Application Publication No. H06-073291) and a composition provided by the mixing and subsequent emulsification of a hydroxyl containing diorganosiloxane and, as a crosslinking agent, a compound selected from linear siloxanes that have the aminoxy group in side chain position, cyclic aminoxysiloxanes, aminoxysilanes, and the partial hydrolysis products of the preceding (refer to Japanese Unexamined Patent Application Publication No. H11-193349) have been proposed. However, these compositions have had the problems of an inadequate strength on the part of the cured film and/or an inadequate adhesiveness to substrate by the cured film.

Oil-in-water silicone emulsion compositions that contain colloidal silica have been introduced in order to solve these problems (refer to Japanese Unexamined Patent Application Publication No. S56-016553, S59-152972, H09-165554, and H10-168393).

However, the conventional colloidal silica containing oil-in-water silicone emulsion compositions have contained a polyorganosiloxane whose degree of polymerization has been increased by the emulsion polymerization during emulsion production of octamethylcyclotetrasiloxane and/or decamethylcyclopentasiloxane using a strong acid or strong base as the polymerization catalyst. A problem with these oil-in-water silicone emulsion compositions has been the presence of large amounts of siloxane oligomers, e.g., octamethylcyclotetrasiloxane, decamethylcyclopentasiloxane, and so forth, in the final product. This problem is due to the simultaneous occurrence of siloxane bond cleavage reactions during the emulsion polymerization with the generation of new low molecular weight polyorganosiloxanes. Due to the volatility of siloxane oligomers such as octamethylcyclotetrasiloxane, decamethylcyclopentasiloxane, and so forth, these oil-in-water silicone emulsions have had the problem of not being usable depending on the particular application.

PRIOR ART DOCUMENTS

Patent Documents

[Patent Document 1] Japanese Unexamined Patent Application Publication No. H06-073291
[Patent Document 2] Japanese Unexamined Patent Application Publication No. H11-193349
[Patent Document 3] Japanese Unexamined Patent Application Publication No. S56-016553
[Patent Document 4] Japanese Unexamined Patent Application Publication No. S59-152972
[Patent Document 5] Japanese Unexamined Patent Application Publication No. H09-165554
[Patent Document 6] Japanese Unexamined Patent Application Publication No. H10-168393

SUMMARY OF THE INVENTION

Technical Problem

An object of the present invention is to provide an oil-in-water silicone emulsion composition that contains little volatile siloxane oligomer, and that, through the removal of water fraction and even without the use of an organotin compound as the curing catalyst, is capable of forming a cured film having rubber elasticity and satisfactory adhesiveness to a substrate.

Solution To Problem

The oil-in-water silicone emulsion composition of the present invention includes (A) 100 mass parts of a polyorganosiloxane that contains in each molecule at least two groups selected from the group consisting of a silicon-bonded hydroxyl group, alkoxy group, and alkoxyalkoxy group, (B) 0.1 to 200 mass parts of a colloidal silica, (C) 0.1 to 100 mass parts of an aminoxy group-containing organosilicon compound that has in each molecule an average of two silicon-bonded aminoxy groups, (D) 1 to 100 mass parts of an ionic emulsifying agent, (E) 0.1 to 50 mass parts of a non-ionic emulsifying agent, and (F) 10 to 500 mass parts of water. The total content of siloxane oligomers comprising 4 to 5 siloxane units in the oil-in-water silicone emulsion composition of the present invention is preferably not more than 2%. In addition, the oil-in-water silicone emulsion composition of the present invention preferably does not contain an organotin compound.

The aforementioned component (A) polyorganosiloxane is preferably a diorganopolysiloxane end blocked at both molecular chain terminals by the hydroxyl group and more preferably has a viscosity at 25° C. from 50 mPa·s to 2,000,000 mPa·s.

The colloidal silica of the aforementioned component (B) is preferably an aqueous dispersion with a pH of 7.0 or higher, that was stabilized by alkali metal ions, ammonium ions or amines.

The aminoxy group-containing organosilicon compound of the aforementioned component (C) is preferably an aminoxy group-containing organosilicon compound represented by the general formula: $R^2R^1{}_2SiO(R^1R^3SiO)_n$ $(R^1_2SiO)_pSiR^1_2R^2$ (wherein $R^1$ is an unsubstituted monovalent hydrocarbyl group or a substituted monovalent hydrocarbyl group; $R^3$ is an aminoxy group; n is 0, 1 or 2; and when n is 0, $R^2$ is an aminoxy group; when n is 1, one of the $R^2$ is an aminoxy group, and the other $R^2$ is a group selected from the group consisting of a monovalent hydrocarbyl group, a hydroxyl group, an alkoxy group, and an alkoxyalkoxy group; when n is 2, $R^2$ is a group selected from the group consisting of a monovalent hydrocarbyl group, a hydroxyl group, an alkoxy group, and an alkoxyalkoxy group; and p is an integer greater than or equal to 0).

The aforementioned component (E) is preferably a polyoxyethylene-polyoxypropylene copolymeric non-ionic emulsifying agent.

The oil-in-water silicone emulsion composition of the present invention preferably additionally comprises, as a component (G), 0.1 to 50 mass parts of an alkoxysilane or alkoxyalkoxysilane represented by $R^1_aSiX_{4-a}$, wherein $R^1$ is an unsubstituted monovalent hydrocarbyl group or a substituted monovalent hydrocarbyl group, X is an alkoxy group or an alkoxyalkoxy group, and a is 0, 1, or 2, or a partial hydrolytic condensation product of the aforementioned alkoxysilane or alkoxyalkoxysilane. The oil-in-water silicone emulsion composition of the present invention also preferably additionally comprises an amine as a component (H). The average particle size of the emulsion particles in the oil-in-water silicone emulsion composition of the present invention is preferably not more than 300 nm.

The method of manufacturing the oil-in-water silicone emulsion composition of the present invention includes the steps of: carrying out emulsification and dispersion on the aforementioned components (A), (C), (D), (E), and a portion of component (F); and compounding component (B) and the remainder of component (F) in the emulsion provided by the preceding step.

The surface treatment method of the present invention carries out a surface treatment on the surface of a substrate with the oil-in-water silicone emulsion composition according to the present invention.

The oil-in-water silicone emulsion composition of the present invention is capable of forming a cured film by removing water fraction, even without the use of an organotin compound as the curing catalyst, and the formed cured film has good surface hardness without tackiness, rubbery elasticity, superior elongation, and satisfactory adhesiveness to a substrate. In particular, it comprises an aminoxy group-containing organosilicon compound that has an average of two silicon-bonded aminoxy groups per molecule, so the formed cured film not only has good surface hardness without tackiness, but also superior elongation, so it can be expected that there will be improved followability of the formed cured film to a deformation of a substrate when a flexible substrate is subjected to surface treatment by using the composition of the present invention. In addition, the oil-in-water silicone emulsion composition of the present invention is prepared by emulsifying polyorganosiloxane that has at least two groups per molecule of a silicon-bonded hydroxyl group or a specific hydrolysable group, so there is a low content of volatile siloxane oligomers such as octamethylcyclotetrasiloxane, decamethylcyclopentasiloxane, and so forth, and it comprises no organotin compound, so it can be used in a wide variety of applications. Also, because oil-in-water silicone emulsion composition of the present invention comprises an aminoxy group-containing organosilicon compound that has an average of two silicon-bonded aminoxy groups per molecule, so gel neither adheres to nor is deposited on production equipment during emulsification.

The method of the present invention for manufacturing the oil-in-water silicone emulsion composition of the present invention can efficiently manufacture this oil-in-water silicone emulsion composition. The method of the present invention for treating a surface can efficiently form a cured silicone film that exhibits a sufficient strength, i.e., a satisfactory rubbery elasticity, and a sufficient adhesiveness to a substrate, on a wide variety of substrate surfaces.

DESCRIPTION OF EMBODIMENTS

Component (A) is a polyorganosiloxane that contains in each molecule at least two groups selected from the group consisting of the silicon-bonded hydroxyl group, silicon-bonded alkoxy groups, and silicon-bonded alkoxyalkoxy groups, and is the base component of the oil-in-water silicone emulsion composition of the present invention. The molecular structure of the component (A) polyorganosiloxane may be straight chain, cyclic, branched, dendritic, or network, but a straight chain or a partially branched straight chain is preferred. The groups selected from the group consisting of the hydroxyl group, alkoxy groups, and alkoxyalkoxy groups may be present in terminal position on the molecular chain or in side chain position on the molecular chain or in both positions. The alkoxy group is preferably an alkoxy group having from 1 to 10 carbon atoms, e.g., methoxy group, ethoxy group, n-propoxy group, isopropoxy group, n-butoxy group, t-butoxy group, hexyloxy group, cyclohexyloxy group, octyloxy group, decyloxy group, and so forth, while the alkoxyalkoxy group is preferably an alkoxyalkoxy group having from 2 to 10 carbon atoms, e.g., methoxymethoxy group, methoxyethoxy group, ethoxymethoxy group, methoxypropoxy group, and so forth.

Unsubstituted monovalent hydrocarbyl groups and substituted monovalent hydrocarbyl groups are examples of the silicon-bonded organic groups other than the groups selected from the group consisting of the hydroxyl group, alkoxy groups, and alkoxyalkoxy groups. Unsubstituted monovalent hydrocarbyl groups having from 1 to 10 carbon atoms are preferred for the unsubstituted monovalent hydrocarbyl groups from the standpoint of the emulsification boosting action. The unsubstituted monovalent hydrocarbyl can be exemplified by alkyl groups having from 1 to 10 carbon atoms such as methyl group, ethyl group, n-propyl group, isopropyl group, butyl group, t-butyl group, hexyl group, octyl group, decyl group, and so forth; cycloalkyl groups having from 3 to 10 carbon atoms such as cyclopentyl group, cyclohexyl group, and so forth; alkenyl groups having from 2 to 10 carbon atoms such as vinyl group, allyl group, 5-hexenyl group, 9-decenyl group, and so forth; aryl groups having from 6 to 10 carbon atoms such as phenyl group, tolyl group, xylyl group, and so forth; and aralkyl groups having from 7 to 10 carbon atoms such as benzyl group, methylbenzyl group, phenethyl group, and so forth. Preferred thereamong are alkyl group, alkenyl group, and aryl group, wherein methyl group and phenyl group are particularly preferred.

The substituted monovalent hydrocarbyl group can be exemplified by groups provided by replacing all or a portion of the hydrogen atoms in the aforementioned unsubstituted monovalent hydrocarbyl groups, and particularly in the alkyl group having from 1 to 10 carbon atoms or phenyl group, with a halogen atom such as fluorine, chlorine, and so forth; an epoxy functional group such as glycidyloxy group, epoxycyclohexyl group, and so forth; a methacrylic functional group such as methacryloxy group and so forth; an acrylic functional group such as acryloxy group and so forth; an amino functional group such as the amino group, aminoethylamino group, phenylamino group, dibutylamino group, and so forth; a sulfur containing functional group such as the mercapto group, the tetrasulfide group, and so forth; or a substituent group such as alkoxy group, hydroxycarbonyl group, alkoxycarbonyl group, and so forth.

The followings are specific examples of the substituted monovalent hydrocarbyl group: 3,3,3-trifluoropropyl group, perfluorobutylethyl group, perfluorooctylethyl group, 3-chloropropyl group, 3-glycidyloxypropyl group, 2-(3,4-epoxycyclohexyl)ethyl group, 5,6-epoxyhexyl group, 9,10-epoxydecyl group, 3-methacryloxypropyl group, 3-acryloxypropyl group, 11-methacryloxy undecyl group, 3-aminopropyl group, N-(2-aminoethyl)aminopropyl group, 3-(N-phenylamino)propyl group, 3-dibutylaminopropyl group, 3-mercaptopropyl group, 3-hydroxycarbonylpropyl group, methoxypropyl group, and ethoxypropyl group.

The viscosity of component (A) at 25° C. is not particularly limited; however, taking into consideration the strength and adhesiveness to substrate of the cured film provided by the oil-in-water silicone emulsion composition of the present invention, the handling characteristics during production of the oil-in-water silicone emulsion composition of the present invention, and the particle size and stability of the oil-in-water silicone emulsion composition of the present invention, component (A) has a viscosity at 25° C. preferably of 50 mPa·s to 2,000,000 mPa·s, more preferably of 100 mPa·s to 500,000 mPa·s, and even more preferably of 500 mPa·s to 100,000 mPa·s.

Component (A) is preferably a diorganopolysiloxane that is end blocked at both molecular chain terminals by the hydroxyl group. Such a diorganopolysiloxane end blocked at both molecular chain terminals by the hydroxyl group can be exemplified by a polyorganosiloxane represented by the general formula $HO(R^1_2SiO)_mH$. $R^1$ in this formula denotes the same silicon-bonded unsubstituted or substituted monovalent hydrocarbyl groups other than the hydroxyl or hydrolyzable groups as described above, wherein alkyl group having from 1 to 10 carbon atoms, aryl group having from 6 to 10 carbon atoms, and alkenyl group having from 2 to 10 carbon atoms are preferred and methyl group and phenyl group are particularly preferred. The subscript m is an integer with a value of at least 2 and preferably is a number that provides a viscosity at 25° C. from 50 mPa·s to 2,000,000 mPa·s.

The component (B) colloidal silica improves the strength of the cured film and improves the adhesiveness of the cured film to substrate. Colloidal silica is obtainable as an aqueous dispersion by colloidally dispersing from 5 to 40 wt. % of silica particles in water. It has many silanol groups on its surface, and the particle diameter generally is from about 1 nm to 1 μm. The preferable such colloidal silica is a basic aqueous dispersion stabilized by using sodium ions, potassium ions, and other alkali metal ions; ammonium ions; amines, and so forth. Of these, it preferably is a basic aqueous dispersion stabilized by using sodium ions or ammonium ions. The pH of the colloidal silica as a basic aqueous dispersion is preferably at least 7.0, and more preferably exceeds 9.0. The shape of the silica microparticles of the colloidal silica is not particularly limited, and is generally spherical. However, one with an elongated shape or a pearl necklace shape can also be used. Component (B) is compounded at preferably 0.1 to 200 mass parts and more preferably at 1 to 100 mass parts, in each case per 100 mass parts component (A).

Specific examples of such colloidal silica are Snowtex 20, Snowtex 30, Snowtex 40, Snowtex 50, Snowtex N, Snowtex S, Snowtex XS, Snowtex 20L, Snowtex ST-XS, Snowtex ST-SS, Snowtex ZL, Snowtex UP, Snowtex PS-S, and Snowtex PS-M manufactured by Nissan Chemical Industries, Ltd.; Adelite AT-20, Adelite AT-30, Adelite AT-20N, Adelite AT-30N, Adelite AT-20A, Adelite AT-30A, Adelite AT-40, Adelite AT-50, Adelite AT-300, and Adelite AT-300S manufactured by Asahi Denka Co., Ltd.; Klebosol 30R9, Klebosol 30R50, and Klebosol 50R50 manufactured by Clariant Japan; Ludox (trademark) HS-40, Ludox HS-30, Ludox LS, and Ludox SM-30 manufactured by DuPont; Cataloid S-20L, Cataloid S-20H, Cataloid S-30L, Cataloid S-30H, Cataloid SI-30, Cataloid SI-40, Cataloid SI-50, Cataloid SI-350, Cataloid SI-500, Cataloid SI-45P, Cataloid SI-80P, Cataloid SA, and Cataloid SC-30 manufactured by Catalysts & Chemicals Industries Co., Ltd.; and Silicadol-20, Silicadol-30, Silicadol-40, Silicadol-305, Silicadol-20AL, Silicadol-20A, Silicadol-20B, Silicadol-20G, and Silicadol-20GA manufactured by Nippon Chemical Industrial Co., Ltd.

The component (C) aminoxy group-containing organosilicon compound promotes the formation of a rubbery elastic cured film having good surface hardness without tackiness by bringing about the reaction and crosslinking of component (A) with itself and/or component (A) with component (B) in the oil-in-water silicone emulsion composition of the present invention. Component (C) contains an average of two silicon-bonded aminoxy groups per molecule. An average of two aminoxy groups can exist only on side molecular chains, and can exist at both molecular terminals, and an average of one aminoxy group can exist at both a molecular terminal and a side molecular chain. It was ascertained that, when an average of 3 or more aminoxy groups are present per molecule in component (C), mixture gelling readily occurs within the emulsification device during emulsification and/or in the premixing process before emulsification, and the gel sometimes adheres to production equipment, and elongation of the obtained cured film is sometimes inferior.

Such aminoxy group-containing organosilicon compound are exemplified by a polydiorganosiloxane end blocked at both molecular chain terminals by an aminoxy group, a diorganosiloxane-organoaminoxysiloxane copolymer end blocked at one molecular chain terminal by an aminoxy group, a diorganosiloxane-organoaminoxysiloxane copolymer end blocked at both molecular chain terminals by a trioganosilyl group, a cyclic diorganosiloxane-organoaminoxysiloxane copolymer, and diaminoxydiorganosilane. Of these, a polydiorganosiloxane end blocked at both molecular chain terminals by an aminoxy group is preferable. The amount of component (C) compounded per 100 mass parts of component (A) is 0.1 to 100 mass parts, preferably 0.5 to 50 mass parts, and more preferably 1 to 20 mass parts.

Component (C) is preferably represented by the general formula

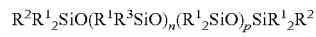

$$R^2R^1_2SiO(R^1R^3SiO)_n(R^1_2SiO)_pSiR^1_2R^2$$

$R^1$ in this formula is the same as previously described, among which alkyl group having from 1 to 10 carbon atoms, aryl group having from 6 to 10 carbon atoms, and alkenyl group having from 2 to 10 carbon atoms are preferred and methyl group and phenyl group are particularly preferred. $R^3$ is an aminoxy group. When n is 0, $R^2$ is an aminoxy group. When n is 1, one of $R^2$ is an aminoxy group, and the remaining $R^2$ is a group selected from the group consisting of an unsubstituted monovalent hydrocarbyl group having from 1 to 10 carbon atoms, a halogen substituted monovalent hydrocarbyl group having from 1 to 10 carbon atoms, a hydroxyl group, an alkoxy group having from 1 to 10 carbons, and an alkoxyalkoxy group having from 2 to 10 carbon atoms. When n is 2, $R^2$ is a group selected from the group consisting of an unsubstituted monovalent hydrocarbyl group having from 1 to 10 carbon atoms, a halogen substituted monovalent hydrocarbyl group having from 1 to 10 carbon atoms, a hydroxyl group, an alkoxy group having from 1 to 10 carbon atoms, and an alkoxyalkoxy group having from 2 to 10 carbon atoms.

The unsubstituted monovalent hydrocarbyl groups can be exemplified by the same groups as provided above, among which alkyl group having from 1 to 10 carbon atoms, aryl group having from 6 to 10 carbon atoms, and alkenyl group having from 2 to 10 carbon atoms are preferred, and methyl group and phenyl group are particularly preferred. The halogen substituted monovalent hydrocarbyl groups can be exemplified by groups provided by substituting halogen for all or a portion of the hydrogen atoms in the aforementioned unsubstituted monovalent hydrocarbyl groups, wherein halogen substituted alkyl group is preferred, e.g., chloromethyl group, 3,3,3-trifluoropropyl group, 3,3,4,4,5,5,5-heptafluoropentyl group, difluoromonochloropropyl group, and so forth. The alkoxy and alkoxyalkoxy groups can be exemplified by the same groups as previously described.

The aminoxy group can be exemplified by a group selected from among those represented by the following formula and —ON(R$^4$)$_2$.

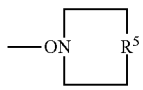

In the formula, R$^4$ is a straight chain or branched alkyl group having from 1 to 5 carbon atoms. In the formula, R$^5$ is a divalent hydrocarbon group having from 2 to 15 carbon atoms, or a divalent organic group having a molecular chain backbone that includes 3 to 17 carbon atoms and 1 to 3 nitrogen atoms or 1 to 2 oxygen atoms; and it is exemplified by —(CH$_2$)$_2$—, —(CH$_2$)$_5$—, —(CH$_2$)$_6$—, —(CH$_2$)$_7$—, —(CH$_2$)$_2$—O—(CH$_2$)$_2$—, —(CH=CH)—(CH=CH)—, —(CH=N)—(CH=CH)—, and —(C$_6$H$_4$)—(CH$_2$)$_2$—. Of these, —(CH$_2$)$_6$— and —(CH$_2$)$_2$—O—(CH$_2$)$_2$— are preferable. Among these, a dialkyl aminoxy group wherein an alkyl group having from 1 to 5 carbon atoms is bonded to a nitrogen atom is preferable; the preferable aminoxy group is exemplified by, for example, a dimethyl aminoxy group, diethyl aminoxy group, dipropyl aminoxy group, dibutyl aminoxy group, diheptyl aminoxy group, ethylmethyl aminoxy group, propylmethyl aminoxy group, propylethyl aminoxy group, butylmethyl aminoxy group, butylethyl aminoxy group, butylpropyl aminoxy group, heptylmethyl aminoxy group, heptylethyl aminoxy group, heptylpropyl aminoxy group, and heptylbutyl aminoxy group, and is preferably a diethyl aminoxy group.

Moreover, in the above formula, n is 0, 1 or 2, preferably 0 or 2, and more preferably 0. When n is 0, R$^2$ in the above formula is an aminoxy group; when n is 1, at least one of the R$^2$ groups is an aminoxy group. Of these, in the above formula, n is preferably 0 and R$^2$ is preferably an aminoxy group, from the standpoint of availability.

In the above formulas, p is an integer greater than or equal to 0, and the upper limit of p is not particularly limited. However, for ease of emulsification, p is preferably an integer in the range from 0 to 1000, more preferably an integer in the range from 2 to 200, and most preferably an integer from 4 to 140.

The aminoxy group-containing organosilicon compound under consideration can be exemplified by the aminoxy group-containing organosilicon compounds given by the following formulas. In these formulas, Me denotes the methyl group; Et denotes the ethyl group; and Pr denotes the propyl group.

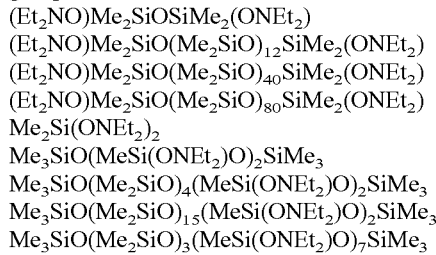

The component (D) ionic emulsifying agent and component (E) non-ionic emulsifying agent bring about a stable emulsification of component (A) and the optional component (G) in component (F). One feature is that the combination use of component (D) and component (E) results in superior storage stability of the obtained oil-in-water emulsion composition, even after compounding component (B). Component (D) is compounded at from 1 to 100 mass parts, preferably from 1 to 50 mass parts, and more preferably from 1 to 20 mass parts, in each case per 100 mass parts component (A).

An anionic surfactant, a cationic surfactant, and an amphoteric surfactant can be used as the component (D) ionic emulsifying agent. A single type of surfactant may be used, or two or more surfactants of different type may be used in combination as the ionic emulsifying agent.

The anionic surfactant can be exemplified by alkylbenzenesulfonate salts, alkyl ether sulfate salts, polyoxyethylene alkyl ether sulfate salts, polyoxyethylene alkylphenyl ether sulfate salts, alkylnaphthylsulfonate salts, unsaturated aliphatic sulfonate salts, and hydroxylated aliphatic sulfonate salts. The alkyl group referenced here can be exemplified by medium and higher alkyl groups such as decyl group, undecyl group, dodecyl group, tridecyl group, tetradecyl group, cetyl group, stearyl group, and so forth. The unsaturated aliphatic group can be exemplified by oleyl group, nonenyl group, and octynyl group. The counterion can be exemplified by the sodium ion, potassium ion, lithium ion, and ammonium ion, with the sodium ion being typically used among these.

The cationic surfactant can be exemplified by quaternary ammonium salt type surfactants such as alkyltrimethylammonium salts, e.g., octadecyltrimethylammonium chloride, hexadecyltrimethylammonium chloride, and so forth, and dialkyldimethylammonium salts, e.g., dioctadecyldimethylammonium chloride, dihexadecyldimethylammonium chloride, didecyldimethylammonium chloride, and so forth.

The amphoteric surfactant can be exemplified by alkylbetaines and alkylimidazolines.

A nonionic surfactant can be used as the non-ionic emulsifying agent of component (E). The nonionic surfactant can be exemplified by glycerol fatty acid esters, sorbitan fatty acid esters, polyoxyalkylene alkyl ethers, polyoxyalkylene alkylphenyl ethers, polyoxyalkylene sorbitan fatty acid esters, polyoxyalkylene glycerol fatty acid esters, and polyoxyethylene-polyoxypropylene copolymer-type nonionic emulsifying agents. The alkyl group referenced here can be exemplified by higher alkyl groups such as decyl group, undecyl group, dodecyl group, tridecyl group, tetradecyl group, cetyl group, stearyl group, and so forth. The fatty acid can be exemplified by medium and higher fatty acids such lauric acid, palmitic acid, stearic acid, oleic acid, and so forth.

Of these, the polyoxyethylene-polyoxypropylene copolymeric non-ionic emulsifying agent is preferable. The polyoxyethylene-polyoxypropylene copolymeric non-ionic emulsifying agent is usually represented by the following general formula (1) or general formula (2).

$$HO(CH_2CH_2O)_a(CH(CH_3)CH_2O)_b(CH_2CH_2O)_cH \quad (1)$$

$$HO(CH(CH_3)CH_2O)_d(CH_2CH_2O)_e(CH(CH_3)CH_2O)_fH \quad (2)$$

In general formulas (1) and (2), a, b, c, d, e, and f are the average number of added moles of ethyleneoxide or propyleneoxide, and are each independently a number from 1 to 350. The weight average molecular weight of component (E) is preferably from 1,000 to 18,000, and more preferably from 1,500 to 10,000. When component (E) is a solid, it can also be used in the form of an aqueous solution.

Such polyoxyethylene-polyoxypropylene copolymeric non-ionic emulsifying agents are specifically exemplified by "Pluronic L" series, "Pluronic P" series, "Pluronic F" series, and "Pluronic TR" series manufactured by Adeka Corporation; Emulgen PP-290 manufactured by Kao Corp.; and Newcol 3240 manufactured by Nippon Nyukazai Co., Ltd.

Component (E) is compounded at from 0.1 to 50 mass parts and preferably from 1 to 20 mass parts, in each case per 100 mass parts component (A). It has been observed that component (E) acts cooperatively with component (D) to reduce the particle size of the emulsion particles.

The total of the compounded amount of component (D) and component (E) is generally preferably from 1 to 30 mass %, and more preferably from 2 to 20 mass % of the total amount of component (A) and the optionally compounded component (G). The ratio between the compounded amount of component (D) and the compounded amount of component (E) is preferably in the range from 3:1 to 100:1.

The component (F) water preferably does not contain a component that interferes with emulsification or the storage stability of the emulsion, and is exemplified by ion exchanged water, distilled water, well water, and tap water. Component (F) is used in an amount sufficient for maintaining a stable water based emulsion state, but the compounded amount is not otherwise particularly limited. However, component (F) is ordinarily compounded at from 10 to 500 mass parts, preferably from 10 to 200 mass parts per 100 mass parts component (A).

Viewed from the perspective of improving the strength of the cured film and its adhesiveness to a substrate, the oil-in-water silicone emulsion of the present invention preferably also comprises (G) an alkoxysilane or alkoxyalkoxysilane represented by the general formula: $R^1{}_aSiX_{4-a}$, or a partial hydrolytic condensation product of such an alkoxysilane or alkoxyalkoxysilane. $R^1$ in the formula is the same as previously described, among which alkyl group having from 1 to 10 carbon atoms, alkenyl group having from 2 to 10 carbon atoms, and aryl group having from 6 to 10 carbon atoms are preferred with methyl group and phenyl group being particularly preferred. X is an alkoxy group having from 1 to 10 carbon atoms, such as a methoxy group, ethoxy group, n-propoxy group, isopropoxy group, n-butoxy group, t-butoxy group, hexyloxy group, cyclohexyloxy group, octyloxy group, and decyloxy group, and so forth; and an alkoxyalkoxy group having from 2 to 10 carbon atoms, such as a methoxymethoxy group, methoxyethoxy group, ethoxymethoxy group, methoxypropoxy group, and so forth. a is 0, 1 or 2.

Specific examples of preferred alkoxysilanes are tetraalkoxysilanes such as tetraethoxysilane, tetrapropoxysilane, and so forth; alkyltrialkoxysilanes such as methyltrimethoxysilane, methyltriethoxysilane, methyltripropoxysilane, ethyltrimethoxysilane, ethyltriethoxysilane, hexyltrimethoxysilane, octyltriethoxysilane, tetradecyltriethoxysilane, and so forth; alkenyltrialkoxysilanes such as allyltrimethoxysilane, vinyltrimethoxysilane, vinyltriethoxysilane, and so forth; aryltrialkoxysilanes such as phenyltrimethoxysilane, phenyltriethoxysilane, and so forth; dialkyldialkoxysilanes such as dimethyldimethoxysilane, dimethyldiethoxysilane, diethyldimethoxysilane, diethyldiethoxysilane, methylethyldimethoxysilane, octylmethyldiethoxysilane, tetradecylmethyldiethoxysilane, and so forth; aryldialkoxysilanes such as phenylmethyldimethoxysilane, diphenyldimethoxysilane, phenylmethyldiethoxysilane, diphenyldiethoxysilane, and so forth; and alkoxysilanes wherein a portion or all of the hydrogen atoms in the phenyl group or alkyl group of the aforementioned alkoxysilanes are replaced with such substituted groups as halogen atoms such as fluorine, chlorine, and so forth; epoxy functional groups such as a glycidyloxy group, an epoxycyclohexyl group, and so forth; methacryl functional groups such as a methacryloxy group, and so forth; acryl functional groups such as an acryloxy group and so forth; amino functional groups such as an amino group, aminoethylamino group, phenylamino group, dibutylamino group, and so forth; sulfur containing functional groups such as a mercapto group, tetrasulfide group, and so forth; alkoxy groups; hydroxycarbonyl groups; and alkoxycarbonyl groups.

Examples of preferred alkoxyalkoxysilanes are those wherein an alkoxyalkoxy group such as a methoxymethoxy group, ethoxyethoxy group, methoxyethoxy group, ethoxymethoxy group, and so forth, is substituted for the alkoxy group of the aforementioned alkoxysilane.

Component (G) is preferably compounded at 0.1 to 50 mass parts and more preferably at 1 to 15 mass parts, in each case per 100 mass parts component (A). When the compounded amount of component (G) is within the aforementioned range, the strength of the cured film of the aqueous emulsion and its adhesiveness to a substrate tend to steadily improve.

In addition, the oil-in-water silicone emulsion composition of the present invention can comprise other components on an optional basis as appropriate, for example, a thickener, antifoaming agent, penetrating agent, antistatic agent, inorganic powder, preservative, anticorrosion agent, silane coupling agent other than component (G), such as bis(trimethoxysilylpropyl)-disulfide, pH adjusting agent, buffer, ultraviolet absorber, tin free curing catalyst, water-soluble resin, organic resin emulsion, pigment, dye, antimicrobial, deodorant, and so forth.

Among the preceding, the use of an amine compound (H) as a pH adjusting agent is preferred. The amine compound can be exemplified by diethylamine, ethylenediamine, butylamine, hexylamine, morpholine, monoethanolamine, triethylamine, triethanolamine, dipropanolamine, 2-amino-2-methyl-2-propanol, and polyethylene imine, wherein diethylamine is preferred among the preceding. The compounded amount of component (H) as the pH adjusting agent is preferably in the range from 0.01 to 5 mass % and is more preferably in the range from 0.1 to 2 mass %.

The oil-in-water silicone emulsion composition of the present invention can be manufactured by a production method comprising the steps of (I): carrying out emulsification and dispersion on component (A), component (C), component (D), component (E), and a portion of component (F), by using an emulsifying device such as a homomixer, homogenizer, colloid mill, Combi mixer, inline type continuous emulsifying device, vacuum emulsifying device, ultrasound emulsifying device, continuous mixing device, and so forth; and (II): compounding and dispersing component (B) and the remainder of component (F) in the emulsion provided by the preceding step. Component (G) may optionally be compounded in either step or may be subdivided and compounded in each step. Viewed from the perspective of the stability of the emulsion composition upon dilution with water, the average particle size of the emulsion particles is preferably not more than 500 nm and is more preferably not more than 300 nm. The average particle size of the emulsion particles can be measured, for example, by a dynamic light scattering procedure.

The total content of siloxane oligomers comprising 4 to 5 siloxane units is preferably not more than 2 mass % in the oil-in-water silicone emulsion composition of the present invention and more preferably is not more than 1 mass % and even more preferably is not more than 0.5 mass %. The siloxane oligomers comprising 4 to 5 siloxane units can be exemplified by tetrameric to pentameric cyclic siloxane oligomers such as octaorganotetracyclosiloxane, decaorganopentacyclosiloxane, and so forth, and by tetrameric to pentameric straight chain siloxane oligomers such as a tetraorganodisiloxane end blocked at both molecular chain terminals by a hydroxydiorganosiloxy group, a hexaorganotrisiloxane end blocked at both molecular chain terminals by a hydroxydiorganosiloxy group, and so forth. The siloxane oligomer content in the oil-in-water silicone emulsion composition of the present invention can be measured by gas chromatography.

The surface treatment method of the present invention includes carrying out a surface treatment on the surface of a substrate with the oil-in-water silicone emulsion composition of the present invention. Although the substrate is not particularly limited, it is exemplified by metals, ceramics, concrete, paper, fibers, natural fiber fabrics, synthetic fiber fabrics, nonwoven fabrics, plastics, glass, rubber, and composites thereof.

The method of carrying out a surface treatment on the surface of a substrate with the aforementioned oil-in-water silicone emulsion composition preferably includes (I) a step of coating the surface of the substrate with the oil-in-water silicone emulsion composition and (II) a step of removing the water in the oil-in-water silicone emulsion composition on the substrate surface to form a cured film on the substrate surface. The specific procedure for carrying out step (I) can be exemplified by spraying, dipping, gravure coating, and knife coating. The water fraction removal in step (II) can be carried out by air drying by standing at ambient temperature; or by standing at an ambient temperature adjusted to 20 to 200° C.; or by exposure to infrared radiation, ultraviolet radiation, or other high energy radiation.

The use of the surface treatment method of the present invention can give to various substrate surfaces a water repellency, weather resistance, chemical resistance, soft texture, and so forth, attributable to silicone elastomers.

EXAMPLE

Next, the present invention will be described in detail based on Practical Examples and Comparative Examples, but the present invention described in the claims is not limited to these Practical Examples. The viscosity in the examples is the value measured at 25° C.; the parts used to indicate the compounded amount denotes mass parts; and the % used to indicate content denotes mass %. In the formulas, Me refers to the methyl group and Et refers to the ethyl group.

The average particle size of the emulsion particles was measured by dynamic light scattering using a submicron particle analyzer (Coulter Model N4 MD from Coulter Electronics, Inc.) at 25° C. and was determined by monodisperse mode analysis. All obtained emulsions were stable, and no separation was observed for 6 months at 25° C.

The strength of the cured film was evaluated by coating a glass panel with an oil-in-water emulsion composition that was prepared and then stored for 5 days at 25° C., letting this stand for 1 day at 25° C. to remove the water fraction, and then touching the film with a finger. Evaluation result was expressed as a number from 1 to 4, based on the following criteria:
1: The cured film had good surface hardness without tackiness, and plastic deformation and peel-off from a glass panel were not observed after rubbing the cured film with a finger.
2: The cured film surface was somewhat soft, but no plastic deformation or peel-off from a glass panel was observed after rubbing the cured film with a finger.
3: The cured film surface was soft and sticky, and plastic deformation was observed after rubbing with a finger, but no peel-off from a glass panel was observed.
4: A film was not sufficiently cured, became a soft and strongly sticky film without elasticity, and peeled easily from a glass panel.

An oil-in-water emulsion composition was prepared and stored for 5 days at room temperature. The composition was applied to a fluororesin panel, which was then left standing for 1 day at 25° C., to remove the water fraction. The cured film was peeled off and cut into strips having a width of 2 cm, to yield test pieces. To evaluate the elongation of the cured film, the obtained test pieces were stretched to the breaking point, which was considered to be their elongation. The test piece thickness was about 1 mm. Evaluation result was expressed as a number from 1 to 4, based on the following criteria:
1: Elongation at test piece breakage was at least 400%.
2: Elongation at test piece breakage was at least 100% and less than 400%.
3: Elongation at test piece breakage was less than 100%.
4: The cured film was unsatisfactorily formed, and test pieces could not be obtained because the film fell apart when peeling test pieces from a fluororesin panel and the like.

An oil-in-water emulsion composition was prepared and stored for 5 days at room temperature. The composition was applied to a fluororesin panel, which was then left standing for 1 day at 25° C., to remove the water fraction. Then, the cured film was peeled off, thereby yielding cured film with a thickness of about 1 mm. The following methods were used to measure its hardness, tensile strength, and breaking elongation.

<Hardness (JIS Type A)>
Cured film was piled up to a thickness of 6 mm, and the type A durometer specified in JIS K6253 was used for measurement.

<Tensile Strength, Breaking Elongation>
Measured in accordance with JIS K6251.

The total content of siloxane oligomers comprising 4 to 5 siloxane units in the prepared oil-in-water silicone emulsion was measured by weighing out a 1.0 g sample; adding 5 ml methanol, 10 ml hexane, and 10 µl n-undecane and stirring for several minutes; thereafter holding at quiescence overnight and then adding 5 ml ultrapure water gently; and subsequently taking the hexane layer and performing the measurement with a gas chromatograph (GC-2010 from Shimadzu). As a result, the content of the aforementioned siloxane oligomer in the oil-in-water emulsion prepared in all Practical Examples and Comparative Examples described below was 0.1%.

In addition, the inside of the continuous mixing device used for emulsification was visually examined. When no gel adherence was found, the evaluation was "No". When obvious gel adherence was found, the evaluation was "Yes".

Practical Example 1

38.0 parts of a polydimethylsiloxane end blocked at both molecular chain terminals by a hydroxydimethylsiloxy group (viscosity: 2,400 mPa·s), 2.0 parts of the aminoxy group-containing polysiloxane represented by formula (1): $Et_2NO(Me_2SiO)_7NEt_2$, 2 parts of a polyoxyethylene-polyoxypropylene copolymeric non-ionic emulsifying agent (trade name: Pluronic F108, manufactured by Adeka Corporation), and 5.4 parts of a 37% aqueous solution of an alpha-olefin sulfonate sodium salt that had about 14 carbon atoms were uniformly mixed, put into a continuous mixing device, and emulsified. After diluting the obtained emulsion with 18.1 parts of water and 33.0 parts of colloidal silica (trade name: Snowtex 30, manufactured by Nissan Chemical Industries, Ltd.; effective ingredient=30%; pH=10; a surface stabilized by sodium), 0.5 part of diethylamine as a pH adjusting agent was added. Furthermore, 1.0 part of methyltriethoxysilane was added, and this was uniformly mixed to prepare an oil-in-water silicone emulsion.

The average particle size of the emulsion particles of the obtained oil-in-water silicone emulsion and the strength and elongation of the cured film are listed in Table 1.

Practical Example 2

An oil-in-water silicone emulsion was prepared by the same procedure as in Practical Example 1, but in this case changing the 1 part of methyltriethoxysilane of Practical Example 1 to 1 part of 3-methacryloxypropylmethyldimethoxysilane.

The evaluation results of the average particle size of the emulsion particles of the obtained oil-in-water silicone emulsion and the strength and elongation of the cured film are listed in Table 1.

Practical Example 3

An oil-in-water silicone emulsion was prepared by the same procedure as in Practical Example 1, but in this case changing the 1 part of methyltriethoxysilane of Practical Example 1 to 1 part of vinyltrimethoxysilane.

The evaluation results of the average particle size of the emulsion particles of the obtained oil-in-water silicone emulsion and the strength and elongation of the cured film are listed in Table 1.

Practical Example 4

An oil-in-water silicone emulsion was prepared by the same procedure as in Practical Example 1, but in this case changing the 1 part of methyltriethoxysilane of Practical Example 1 to 1 part of 3-glycidoxypropyltrimethoxysilane.

The evaluation results of the average particle size of the emulsion particles of the obtained oil-in-water silicone emulsion and the strength and elongation of the cured film are listed in Table 1.

Practical Example 5

An oil-in-water silicone emulsion was prepared by the same procedure as in Practical Example 1, but in this case changing the 1 part of methyltriethoxysilane of Practical Example 1 to 1 part of 3-mercaptopropyltriethoxysilane.

The evaluation results of the average particle size of the emulsion particles of the obtained oil-in-water silicone emulsion and the strength and elongation of the cured film are listed in Table 1.

Practical Example 6

38.0 parts of a polydimethylsiloxane end blocked at both molecular chain terminals by a hydroxydimethylsiloxy group (viscosity: 2,400 mPa·s), 2.0 parts of the aminoxy group-containing polysiloxane represented by formula (2): $Et_2NO(Me_2SiO)_{14}NEt_2$, 1.5 parts of a polyoxyethylene-polyoxypropylene copolymeric non-ionic emulsifying agent (trade name: Pluronic F108, manufactured by Adeka Corporation), and 5.0 parts of a 40% aqueous solution of the monosulfonate sodium salt of normal paraffin that had about 15 carbon atoms were uniformly mixed, put into a continuous mixing device, and emulsified. After diluting the obtained emulsion with 34.4 parts of water and 17.6 parts of colloidal silica (trade name: Snowtex 30, manufactured by Nissan Chemical Industries, Ltd.; effective ingredient=30%; pH=10; a surface stabilized by sodium), 0.5 part of diethylamine as a pH adjusting agent was added. Furthermore, 1.0 part of tetraethoxysilane was added, and this was uniformly mixed to prepare an oil-in-water silicone emulsion.

The evaluation results of the average particle size of the emulsion particles of the obtained oil-in-water silicone emulsion and the strength and elongation of the cured film are listed in Table 1.

Practical Example 7

37.0 parts of a polydimethylsiloxane end blocked at both molecular chain terminals by a hydroxydimethylsiloxy group (viscosity: 2,400 mPa·s), 3.0 parts of the aminoxy group-containing polysiloxane represented by the above formula (2), 2.0 parts of a polyoxyethylene-polyoxypropylene copolymeric non-ionic emulsifying agent (trade name: Pluronic F108, manufactured by Adeka Corporation), and 5.4 parts of a 37% aqueous solution of an alpha-olefin sulfonate sodium salt that had about 14 carbon atoms were uniformly mixed, put into a continuous mixing device, and emulsified. After diluting the obtained emulsion with 17.9 parts of water and 33.0 parts of colloidal silica (trade name: Snowtex 30, manufactured by Nissan Chemical Industries, Ltd.; effective ingredient=30%; pH=10; a surface stabilized by sodium), 0.7 part of diethylamine as a pH adjusting agent was added. Furthermore, 1.0 part of methyltriethoxysilane was added, and this was uniformly mixed to prepare an oil-in-water silicone emulsion.

The evaluation results of the average particle size of the emulsion particles of the obtained oil-in-water silicone emulsion and the strength and elongation of the cured film are listed in Table 1. The hardness (JIS type A) of the obtained cured film was 29; the tensile strength was 2.1 MPa; and the breaking elongation was 840%.

Practical Example 8

38.0 parts of a polydimethylsiloxane end blocked at both molecular chain terminals by a hydroxydimethylsiloxy group (viscosity: 2,400 mPa·s), 2.0 parts of the aminoxy group-containing polysiloxane represented by the above formula (2), 1.0 part of a polyoxyethylene-polyoxypropylene copolymeric non-ionic emulsifying agent (trade name: Pluronic F108, manufactured by Adeka Corporation), 8.0 parts of a 70% aqueous solution of a sodium polyoxyethylene (2) laurylether sulfate, and 3.0 parts of water were uniformly mixed, put into a continuous mixing device, and emulsified. After diluting the obtained emulsion with 22.5 parts of water and 22.0 parts of colloidal silica (trade name: Snowtex 30, manufactured by Nissan Chemical Industries, Ltd.; effective ingredient=30%; pH=10; a surface stabilized by sodium), 2.5 parts of an aqueous solution provided by diluting 0.5 part of diethylamine as a pH adjusting agent with 2 parts of water was added. Furthermore, 1.0 part of methyltriethoxysilane was added, and this was uniformly mixed to prepare an oil-in-water silicone emulsion.

The evaluation results of the average particle size of the emulsion particles of the obtained oil-in-water silicone emulsion and the strength and elongation of the cured film are listed in Table 1.

Comparative Example 1

40.0 parts of a polydimethylsiloxane end blocked at both molecular chain terminals by a hydroxydimethylsiloxy group (viscosity: 2,400 mPa·s), 2 parts of a polyoxyethylene-polyoxypropylene copolymeric non-ionic emulsifying agent (trade name: Pluronic F108, manufactured by Adeka Corporation), 5.4 parts of a 37% aqueous solution of an alpha-olefin sulfonate sodium salt that had about 14 carbon atoms, and 1.6 parts of water were uniformly mixed, put into a continuous mixing device, and emulsified. After diluting the obtained emulsion with 17.3 parts of water and 33.0 parts of colloidal silica (trade name: Snowtex 30, manufactured by Nissan Chemical Industries, Ltd.; effective ingredient=30%; pH=10; a surface stabilized by sodium), 0.7 part of diethylamine as a pH adjusting agent was added and uniformly mixed to prepare an oil-in-water silicone emulsion.

The evaluation results of the average particle size of the emulsion particles of the obtained oil-in-water silicone emulsion and the strength and elongation of the cured film are listed in Table 1.

Comparative Example 2

An oil-in-water silicone emulsion was prepared by the same procedure as in Comparative Example 1, but in this case changing the 17.3 parts of dilution water added after emulsification to 16.3 parts, further adding 1 part of methyltriethoxysilane after the diethylamine was added, and uniformly mixing the mixture.

The evaluation results of the average particle size of the emulsion particles of the obtained oil-in-water silicone emulsion and the strength and elongation of the cured film are listed in Table 1.

Comparative Example 3

38.0 parts of a polydimethylsiloxane end blocked at both molecular chain terminals by a hydroxydimethylsiloxy group (viscosity: 2,400 mPa·s), 2.0 parts of the aminoxy group-containing polysiloxane represented by formula ($^3$): $Me_3SiO(Me_2SiO)_3(MeSi(ONEt_2)O)_5SiMe_3$, 1.0 part of a polyoxyethylene-polyoxypropylene copolymeric non-ionic emulsifying agent (trade name: Pluronic F108, manufactured by Adeka Corporation), 8.0 parts of a 70% aqueous solution of a sodium polyoxyethylene (2 mol) laurylether sulfate, and 3.0 parts of water were uniformly mixed, put into a continuous mixing device, and emulsified. After diluting the obtained emulsion with 11.0 parts of water and 33.0 parts of colloidal silica (trade name: Snowtex C, manufactured by Nissan Chemical Industries, Ltd.; effective ingredient=20%; pH=9; a surface treated by aluminum), 2.5 parts of an aqueous solution provided by diluting 0.5 part of diethylamine as a pH adjusting agent with 2.5 parts of water was added. Furthermore, 1.0 part of a methyltriethoxysilane was added and the mixture was uniformly mixed to prepare an oil-in-water silicone emulsion.

This time, gel adherence was observed inside the continuous mixing device after emulsification.

The evaluation results of the average particle size of the emulsion particles of the obtained oil-in-water silicone emulsion and the strength and elongation of the cured film are listed in Table 1.

TABLE 1

| | Average particle diameter (nm) | Gel adherence | Film strength | Film elongation |
|---|---|---|---|---|
| Practical Example 1 | 210 | No | 1 | 1 |
| Practical Example 2 | 210 | No | 1 | 1 |
| Practical Example 3 | 210 | No | 1 | 1 |
| Practical Example 4 | 210 | No | 1 | 2 |
| Practical Example 5 | 210 | No | 1 | 1 |
| Practical Example 6 | 240 | No | 2 | 1 |
| Practical Example 7 | 200 | No | 1 | 1 |
| Practical Example 8 | 190 | No | 1 | 1 |
| Comparative Example 1 | 220 | No | 2 | 3 |
| Comparative Example 2 | 220 | No | 2 | 3 |
| Comparative Example 3 | 190 | Yes | 2 | 3 |

Practical Example 9

38.0 parts of a polydimethylsiloxane end blocked at both molecular chain terminals by a hydroxydimethylsiloxy group (viscosity: 2,400 mPa·s), 2.0 parts of the aminoxy group-containing polysiloxane represented by the formula (2): $Et_2NO(Me_2SiO)_{14}NEt_2$, 1.5 parts of a polyoxyethylene-polyoxypropylene copolymeric non-ionic emulsifying agent (trade name: Pluronic F108, manufactured by Adeka Corporation), and 5.0 parts of a 40% aqueous solution of the monosulfonate sodium salt of normal paraffin that had about 15 carbon atoms were uniformly mixed, put into a continuous mixing device, and emulsified. After diluting the obtained emulsion with 34.4 parts of water and 17.6 parts of colloidal silica (trade name: Snowtex 30, manufactured by Nissan Chemical Industries, Ltd.; effective ingredient=30%; pH=10; a surface stabilized by sodium), 0.5 part of diethylamine as a pH adjusting agent was added. Furthermore, 1.0 part of 3-methacryloxypropylmethyldimethoxysilane was added, and this was uniformly mixed to prepare an oil-in-water silicone emulsion.

The hardness, tensile strength, and breaking elongation of the film obtained by curing the obtained oil-in-water silicone emulsion are listed in Table 2.

Practical Example 10

38.0 parts of a polydimethylsiloxane end blocked at both molecular chain terminals by a hydroxydimethylsiloxy group (viscosity: 2,400 mPa·s), 2.0 parts of the aminoxy group-containing polysiloxane represented by the formula (2): $Et_2NO(Me_2SiO)_{14}NEt_2$, 2.0 parts of a polyoxyethylene-polyoxypropylene copolymeric non-ionic emulsifying agent (trade name: Pluronic F108, manufactured by Adeka Corporation), 5.4 parts of a 37% aqueous solution of an alpha-olefin sulfonate sodium salt that had about 14 carbon atoms, and 1.6 parts of water were uniformly mixed, put into a continuous mixing device, and emulsified. After diluting the obtained emulsion with 16.5 parts of water and 33.0 parts of colloidal silica (trade name: Snowtex 30, manufactured by Nissan Chemical Industries, Ltd.; effective ingredient=30%; pH=10; a surface stabilized by sodium), 0.5 part of diethylamine as a pH adjusting agent was added. Furthermore, 1.0 part of methyltriethoxysilane was added, and this was uniformly mixed to prepare an oil-in-water silicone emulsion.

The average particle size of the emulsion particles of the obtained oil-in-water silicone emulsion was 200 nm. The hardness, tensile strength, and breaking elongation of the film obtained by curing the obtained oil-in-water silicone emulsion are listed in Table 2.

Practical Example 11

An oil-in-water silicone emulsion was prepared in the same manner as the oil-in-water silicone emulsion of Practical Example 10 with the exceptions that the amount of the polydimethylsiloxane end blocked at both molecular chain terminals by a hydroxydimethylsiloxy group (viscosity=2,400 mPa·s) was changed to 35.0 parts, and the amount of the aminoxy group-containing polysiloxane represented by the formula (2): $Et_2NO(Me_2SiO)_{14}NEt_2$ was changed to 5.0 parts.

The average particle size of the emulsion particles of the obtained oil-in-water silicone emulsion was 210 nm. The hardness, tensile strength, and breaking elongation of the film obtained by curing the obtained oil-in-water silicone emulsion are listed in Table 2.

Practical Example 12

An oil-in-water silicone emulsion was prepared in the same manner as the oil-in-water silicone emulsion of Practical Example 10 with the exceptions that the amount of the polydimethylsiloxane end blocked at both molecular chain terminals by a hydroxydimethylsiloxy group (viscosity=2,400 mPa·s) was changed to 30.0 parts, and the amount of the aminoxy group-containing polysiloxane represented by the formula (2): $Et_2NO(Me_2SiO)_{14}NEt_2$ was changed to 10.0 parts.

The average particle size of the emulsion particles of the obtained oil-in-water silicone emulsion was 200 nm. The hardness, tensile strength, and breaking elongation of the film obtained by curing the obtained oil-in-water silicone emulsion are listed in Table 2.

Practical Example 13

24.0 parts of a polydimethylsiloxane end blocked at both molecular chain terminals by a hydroxydimethylsiloxy group (viscosity: 800 mPa·s), 16.0 parts of the aminoxy group-containing polysiloxane represented by the formula (2): $Et_2NO(Me_2SiO)_{14}NEt_2$, 2.0 parts of a polyoxyethylene-polyoxypropylene copolymeric non-ionic emulsifying agent (trade name: Pluronic F108, manufactured by Adeka Corporation), 5.4 parts of a 37% aqueous solution of an alpha-olefin sulfonate sodium salt that had about 14 carbon atoms, and 2.6 parts of water were uniformly mixed, put into a continuous mixing device, and emulsified. After diluting the obtained emulsion with 34.4 parts of water and 17.6 parts of colloidal silica (trade name: Snowtex 30, manufactured by Nissan Chemical Industries, Ltd.; effective ingredient=30%; pH=10; a surface stabilized by sodium), 0.7 part of diethylamine as a pH adjusting agent was added. Furthermore, 1.0 part of methyltriethoxysilane was added, and this was uniformly mixed to prepare an oil-in-water silicone emulsion.

The hardness, tensile strength, and breaking elongation of the film obtained by curing the obtained oil-in-water silicone emulsion are listed in Table 2.

TABLE 2

|  | Practical Example 9 | Practical Example 10 | Practical Example 11 | Practical Example 12 | Practical Example 13 |
|---|---|---|---|---|---|
| Hardness (JIS type A) | 14 | 34 | 24 | 34 | 27 |
| Tensile strength (MPa) | 0.8 | 1.6 | 1.2 | 1.3 | 1.6 |
| Breaking elongation (%) | 550 | 460 | 810 | 760 | 510 |

Practical Example 14

The oil-in-water emulsion prepared in Practical Example 1 was stored for 5 days at 25° C. The emulsion composition was used to impregnate a polyester fabric. The emulsion-impregnated fabric was left to stand for 1 day at 25° C. to remove the water fraction, thereby yielding a silicone rubber/polyester fabric composite. There was good adherence between the polyester fabric and the silicone rubber of the obtained composite, and no peel-off of the silicone rubber from the polyester fabric was observed even after the crease-flex test.

Practical Example 15

An oil-in-water silicone emulsion was prepared by the same procedure as in Practical Example 1, but in this case changing the 1.0 part of methyltriethoxysilane of Practical Example 1 to 1.0 part of aminoethylaminopropyltriethoxysilane.

After the obtained oil-in-water emulsion was stored for 10 days at 25° C., it was used to coat the surfaces of various substrates: glass, cured silicone rubber piece, cured EPDM piece, polycarbonate resin, and PET resin. These emulsion-coated substrates were left to stand for 1 day at 25° C. to remove the water fraction, and they were touched with a finger to evaluate the adhesiveness of the cured film to substrate and the strength of the cured film. As a result, good adherence was observed for all substrates, and the cured film surfaces had good surface hardness without tackiness.

Industrial Applicability

The oil-in-water silicone emulsion composition of the present invention, when coated on or impregnated in a substrate followed by removal of the water fraction, forms a cured film that has superior adhesiveness to a substrate, good surface hardness without tackiness, and superior rubbery elasticity; i.e., a cured film with superior strength. In addition, the cured film obtained by the oil-in-water silicone emulsion composition of the present invention has superior elongation, so when used as the surface treating agent of a flexible substrate, it exhibits superior followability in response to substrate deformation. For this reason, the oil-in-water silicone emulsion composition of the present invention is useful for water based paints and inks; paper coating agents used in thermal paper, ink jet paper, and so forth; mold release agents for rubber; resin or rubber surface coating agents used for automotive weather stripping, gaskets, rubber hoses, and so forth; treatment agents for textiles; surface coating agents for fabrics, nonwoven fabrics, air-bag fabrics, and so forth; penetrants or surface materials for artificial leather and synthetic leather having a substrate made of a fabric or a nonwoven fabric; binders that support antimicrobials, deodorants, and other function imparting agents on the substrate such as a fabric, nonwoven fabric, and so forth; printing inks for clothing; peeling agents; surface coating agents for construction materials, cosmetics, and the like.

The invention claimed is:

1. An oil-in-water silicone emulsion composition comprising (A) 100 mass parts of a polyorganosiloxane that contains in each molecule at least two groups selected from the group consisting of a silicon-bonded hydroxyl group, alkoxy group, and alkoxyalkoxy group, (B) 0.1 to 200 mass parts of a colloidal silica, (C) 0.1 to 100 mass parts of an aminoxy group-containing organosilicon compound that has in each molecule an average of two silicon-bonded aminoxy groups, (D) 1 to 100 mass parts of an ionic emulsifying agent, (E) 0.1 to 50 mass parts of a polyoxyethylene-polyoxypropylene copolymeric non-ionic emulsifying agent, and (F) 10 to 500 mass parts of water.

2. The oil-in-water silicone emulsion composition according to claim 1, wherein the polyoxyethylene-polyoxypropylene copolymeric non-ionic emulsifying agent is a compound represented by the following general formula (1) or general formula (2):

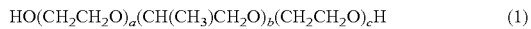

$$HO(CH_2CH_2O)_a(CH(CH_3)CH_2O)_b(CH_2CH_2O)_cH \quad (1)$$

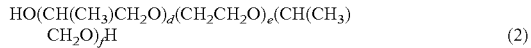

$$HO(CH(CH_3)CH_2O)_d(CH_2CH_2O)_e(CH(CH_3)CH_2O)_fH \quad (2)$$

wherein, a, b, c, d, e, and f are the average number of added moles of ethylene oxide or propylene oxide, and are each independently a number from 1 to 350.

3. The oil-in-water silicone emulsion composition according to claim 1, wherein the polyorganosiloxane of component (A) is a diorganopolysiloxane end blocked at both molecular chain terminals by a hydroxyl group.

4. The oil-in-water silicone emulsion composition according to claim 1, wherein the viscosity of component (A) at 25° C. is from 50 mPa·s to 2,000,000 mPa·s.

5. The oil-in-water silicone emulsion composition according to claim 1, wherein component (B) is an aqueous dispersion with a pH of 7.0 or higher, that is stabilized by alkali metal ions, ammonium ions or amines.

6. The oil-in-water silicone emulsion composition according to claim 1, wherein the aminoxy group-containing organosilicon compound of component (C) is an aminoxy group-containing organosilicon compound represented by the general formula: $R^2R^1{}_2SiO(R^1R^3SiO)_n(R^1{}_2SiO)_pSiR^1{}_2R^2$, wherein $R^1$ is an unsubstituted monovalent hydrocarbyl group or substituted monovalent hydrocarbyl group; $R^3$ is an aminoxy group; n is 0, 1 or 2; when n is 0, $R^2$ is an aminoxy group; when n is 1, one of $R^2$ is an aminoxy group, the other $R^2$ is a group selected from the group consisting of a monovalent hydrocarbyl group, a hydroxyl group, an alkoxy group, and an alkoxyalkoxy group; when n is 2, $R^2$ is a group selected from the group consisting of a monovalent hydrocarbyl group, a hydroxyl group, an alkoxy group, and an alkoxyalkoxy group; and p is an integer greater than or equal to 0.

7. The oil-in-water silicone emulsion composition according to claim 1, wherein the total content of siloxane oligomers comprising 4 to 5 siloxane units is not more than 2 mass%.

8. The oil-in-water silicone emulsion composition according to claim 1, wherein the oil-in-water silicone emulsion composition does not contain an organotin compound.

9. The oil-in-water silicone emulsion composition according to claim 1, further comprising, as a component (G), 0.1 to 50 mass parts of an alkoxysilane or alkoxyalkoxysilane represented by $R^1{}_aSiX_{4-a}$, wherein $R^1$ is an unsubstituted monovalent hydrocarbyl group or a substituted monovalent hydrocarbyl group; X is an alkoxy group or an alkoxyalkoxy group; and a is 0, 1 or 2; or a partial hydrolytic condensation product of the alkoxysilane or the alkoxyalkoxysilane.

10. The oil-in-water silicone emulsion composition according to claim 1, further comprising an amine as a component (H).

11. The oil-in-water silicone emulsion composition according to claim 1, wherein the average particle size of emulsion particles is not more than 300 nm.

12. A method for manufacturing the oil-in-water silicone emulsion composition according to claim 1, comprising the steps of: carrying out emulsification and dispersion on a polyorganosiloxane (A) that contains in each molecule at least two groups selected from the group consisting of a silicon-bonded hydroxyl group, alkoxy group, and alkoxyalkoxy group; an aminoxy group-containing organosilicon compound (C) having in each molecule an average of two silicon-bonded aminoxy groups; an ionic emulsifying agent (D), a polyoxyethylene-polyoxypropylene copolymeric non-ionic emulsifying agent (E), and a portion of water (F) to form a first emulsion; and compounding a colloidal silica (B) and the residual water (F) into the first emulsion to form the oil-in-water emulsion.

13. A method of treating a surface, characterized by carrying out a surface treatment on the surface of a substrate with the oil-in-water silicone emulsion composition according to claim 1.

14. The oil-in-water silicone emulsion composition according to claim 1, wherein the polyorganosiloxane of component (A) is a diorganopolysiloxane end blocked at both molecular chain terminals by a hydroxyl group.

15. The oil-in-water silicone emulsion composition according to claim 2, wherein the polyorganosiloxane of component (A) is a diorganopolysiloxane end blocked at both molecular chain terminals by a hydroxyl group.

16. The oil-in-water silicone emulsion composition according to claim 1, wherein the aminoxy group-containing organosilicon compound of component (C) is an aminoxy group-containing organosilicon compound represented by the general formula: $R^2R^1{}_2SiO(R^1R^3SiO)_n(R^1{}_2SiO)_pSiR^1{}_2R^2$, wherein $R^1$ is an unsubstituted monovalent hydrocarbyl group or substituted monovalent hydrocarbyl group; $R^3$ is an aminoxy group; n is 0, 1 or 2; when n is 0, $R^2$ is an aminoxy group; when n is 1, one of $R^2$ is an aminoxy group, the other $R^2$ is a group selected from the group consisting of a monovalent hydrocarbyl group, a hydroxyl group, an alkoxy group, and an alkoxyalkoxy group; when n is 2, $R^2$ is a group selected from the group consisting of a monovalent hydrocarbyl group, a hydroxyl group, an alkoxy group, and an alkoxyalkoxy group; and p is an integer greater than or equal to 0.

17. The oil-in-water silicone emulsion composition according to claim 4, wherein the aminoxy group-containing organosilicon compound of component (C) is an aminoxy group-containing organosilicon compound represented by the general formula: $R^2R^1{}_2SiO(R^1R^3SiO)_n(R^1{}_2SiO)_pSiR^1{}_2R^2$, wherein $R^1$ is an unsubstituted monovalent hydrocarbyl group or substituted monovalent hydrocarbyl group; $R^3$ is an aminoxy group; n is 0, 1 or 2; when n is 0, $R^2$ is an aminoxy group; when n is 1, one of $R^2$ is an aminoxy group, the other $R^2$ is a group selected from the group consisting of a monovalent hydrocarbyl group, a hydroxyl group, an alkoxy group, and an alkoxyalkoxy group; when n is 2, $R^2$ is a group selected from the group consisting of a monovalent hydrocarbyl group, a hydroxyl group, an alkoxy group, and an alkoxyalkoxy group; and p is an integer greater than or equal to 0.

* * * * *